United States Patent [19]

Kaiser et al.

[11] Patent Number: 5,429,246

[45] Date of Patent: Jul. 4, 1995

[54] PROCESS FOR THE DETECTION OF LIQUIDS IN FIBROUS AND/OR POROUS MATERIALS

[75] Inventors: Dieter Kaiser, Dortmund; Franz Wintrich, Essen, both of Germany

[73] Assignee: RWE Entsorgung, Essen, Germany

[21] Appl. No.: 123,739

[22] Filed: Sep. 20, 1993

[30] Foreign Application Priority Data

Sep. 21, 1992 [DE] Germany ............... 42 31 526.3

[51] Int. Cl.6 ............................................. B07C 5/02
[52] U.S. Cl. ...................................... 209/3.1; 209/11; 209/576
[58] Field of Search .............. 209/3, 3.1, 10, 11, 209/576; 73/73, 74, 75

[56] References Cited

U.S. PATENT DOCUMENTS

| | | | |
|---|---|---|---|
| 5,124,662 | 6/1992 | Downing et al. | 209/576 X |
| 5,125,514 | 6/1992 | Oehler et al. | 209/576 X |
| 5,209,355 | 5/1993 | Mindermann | 209/576 X |

*Primary Examiner*—David H. Bollinger
*Attorney, Agent, or Firm*—Connolly & Hutz

[57] ABSTRACT

The instant invention relates to a process for the detection of liquids in fibrous and/or porous materials by irradiating the materials by a source of microwaves, detecting the heat emission by temperature measuring devices and transmission of the temperature data thus obtained to a sorting device, and controlling the sorting device by the temperature data thus obtained, whereby first the materials are treated with a polymer solution and whereby residual humidity within the materials is detected after curing of the polymer and drying of the material and whereby sorting of materials, which contain residual liquids and of materials which are free of liquids is carried out, based on the differences in temperature increase.

17 Claims, No Drawings

PROCESS FOR THE DETECTION OF LIQUIDS IN FIBROUS AND/OR POROUS MATERIALS

The instant invention relates to a process for the detection of liquids in fibrous and/or porous materials by irradiating the materials by a source of microwaves, detecting the heat emission by temperature measuring devices and transmission of the temperature data thus obtained to a sorting device, and controlling the sorting device by the temperature data thus obtained, whereby first the materials are treated with a polymer solution and whereby residual humidity within the materials is detected after curing of the polymer and drying of the material and whereby sorting of materials, which contain residual liquids and of materials which are free of liquids is carried out, based on the differences in temperature increase.

It is known that materials heat up differently, based on differences in energy absorption and on differences in heat conductivity by irradiating these materials with microwaves.

This effect has been used among other applications in sorting of materials, in particular of waste materials, by measuring the differences in heat emission with the aid of temperature measuring devices and by using the data thus obtained as signals for controlling sorting devices.

In German Patent Application P 40 18 757 a process is disclosed, which permits the identification of electrically non-conductive materials in a mixture of conductive and non-conductive materials.

The process makes it possible, to separate organic waste, for example materials, which can be composted from inorganic materials like glass and metals.

This patent also discloses that the effect of temperature increase and as a consequence of separation can by boosted by wetting the material to be composted, since wetting leads to an increase in heat absorption.

In German Patent Application P 40 21 882 a process for the identification of different types of plastic materials is described.

This process is also based on the irradiation of a mixture of different plastic materials with microwaves, whereby the differences in heat emission are used to operate respectively control a sorting device. For measuring the heat emission preferably a pyrometer is used.

Although the processes described are known, a person skilled in the art still has not succeeded to carry out specific separating processes in various important technical areas. Such an area is sorting out materials, which contain residual humidity and which are produced from rock wool, glass wool, textil materials of various chemical composition and related materials and whose individual components are adhered to each other by the application of aqueous polymer solutions and curing of these solutions. Despite curing, completed polymerization and subsequent drying, part of these materials still may contain residual humidity. If these partially humid materials are used in certain applications, like the application as plaster carrier boards in the building industry, the remaining humidity has a very unfavorable effect.

Object of the instant invention therefore was to identify such materials containing residual humidity and to recycle them by an economical after-treatment process.

Hitherto no process has been available for identification and sorting out of such undesired materials and their after-treatment.

As a consequence a considerable risque existed for the producer and the applyer in using building materials consisting of rock wool, glass wool and related materials.

Applicant now has succeeded in developing a very reliable and economical process for the detection of liquids in fibrous and/or porous materials by irradiating these materials by a source of microwaves, detecting the heat emission from the materials irradiated, by temperature measuring devices and by transmitting the data thus obtained to a sorting device and by controlling the sorting device by the temperature data thus obtained, characterized in that the materials are treated with a polymer solution, that residual humidity within the materials is detected after curing of the polymer and drying of the materials, and that the materials containing residual humidity are separated from the materials, containing no residual humidity, by sorting.

The type of materials, which can be treated by the inventive process, may vary considerably. Such materials may be rock wool, glass wool, ceramic fibers, textile-type materials of different kind and related materials, which are known to a person skilled in the art. Also mixtures of such materials are well suited according to the invention.

The shape of the materials may vary in a wide range, like being fleece-like, cloth-like, mat-like, but the materials may also have the shape of coils, balls, spheres, blocks or intermediate and differently shaped bodies. After single fibers respectively threads, have been produced first by conventional processes for example by spinning through nozzles, extruding etc. the fibers or threads are processed subsequently to the shapes desired, for example by coiling, pressing together and related methods. Finally the fibers or threads of the shaped materials are adhered or connected to each other by spraying them with a curable, preferably aqueous, respectively predominantly aqueous polymer solution and subsequent curing or a final polymerization step. Suitable polymer solutions contain for example not completely cured polymers consisting of formaldehyde and components like phenol and phenol derivatives, melamine and melamine derivatives, urea and urea derivatives, polyacrylates and derivatives, like polymethacrylate and others, which are known to a person skilled in the art. Curing of these materials may be carried out by different methods, for example by simply heating them, but also by adding radical forming additives and other methods.

After drying, the materials are in general ready for use by the end-user.

An important field of application for such materials is the building industry, where they are used as plaster carrier board, insulation boards, boards for wall papers and others. For these applications it is very important, that the materials used, are free of residual humidity, since humidity leads to heavy damages like separation and discoloration of plaster and wall paper.

Therefore it is of great importance for the producer of such materials and also the user of them that residual humidity can be identified during an early stage of the production and application process and that such undesirable materials are sorted out. Furthermore this sorting process must be technically reliable and economical.

According to the state of the art such a process, which excludes damages as described above, still has been missing.

In this situation applicant has succeeded in the development of a very efficient and advantageous process, which solves the problems described above. Although irradiation as such with microwaves is known, by application of microwaves in the field of the invention, which results in different uptake of heat by dry areas and areas with residual humidity, detection of the heat emission from the materials irradiated, by a temperature measuring device, like a thermo-couple or several thermocouples, or a pyrometer or by other devices which are sensitive to heat, and transmission of the temperature data to a computer stored with comparative data, the materials, which still contain residual humidity can be clearly identified. Transmission of signals from the computer to a sorting device, very reliably leads to the separation of the undesired materials.

Identification and sorting according to the invention can also be used to operate a cutting machine, which cuts off the areas, which contain residual humidity, followed by separation of these areas.

Subsequently the materials separated by sorting can be recycled and fed into a drying device.

Beyond that the inventive process makes it possible, to determine the quantity of residual humidity by measuring the size of the humide area in carrying out measurements for heat emission from at least two directions, preferably from above and below the material. With the aid of computerized comparative data this measuring method permits to determine quantitatively the quantity of residual humidity, in particular of water. The measurements can also be made in more then two directions according to the invention. However, in general, measurements from two directions are sufficient.

The reliable determination of the quantity of water permits to carry out drying of the materials, which still contain residual humidity, precisely, with the result that no more energy is used as actually necessary for removal of the humidity.

Although basicly humidity can also be identified, which doesn't consist of water or not exclusively of water, identification of water is of predominant importance, since in general, aqueous polymer solutions are used for adhering and connecting fibrous and porous materials as described above.

Other solvents may be of some importance, if areas, which contain such solvents can also be identified by using microwaves and differences in heat emission. Solvents are preferred, which don't form explosive mixtures with air.

We claim:

1. A process for removing from fibrous and/or porous material those portions of said material which contain residual humidity, said process comprising:
    selecting as the fibrous and/or porous material a processed material which has been processed by applying to it a curable polymer, then curing and drying the curable polymer, said processed material, despite the curing and drying, having a tendency to contain residual humidity,
    irradiating said processed material by means of a source of microwaves,
    detecting portions of said irradiated, processed material containing residual humidity by detecting, with a temperature measuring device, the heat emission from the processed material thus irradiated,
    transmitting temperature data from said temperature measuring device to a sorting device controlled by the temperature data, and
    with said sorting device, removing from said irradiated, processed material the thus-detected portions of said material which contain residual humidity.

2. Process according to claim 1, wherein said processed material has been processed by applying to a it a polymer solution, which polymer solution has been cured and dried.

3. Process according to claim 2, wherein said polymer solution is an aqueous polymer solution.

4. Process according to claim 3, wherein said aqueous polymer solution has not been completely cured and contains formaldehyde.

5. Process according to claim 3, wherein said aqueous polymer solution has not been completely cured and contains a polyacrylate or polyacrylate derivative.

6. Process according to claim 1, wherein said processed material comprises rock wool.

7. Process according to claim 1, wherein said processed material comprises glass wool.

8. Process according to claim 1, wherein said processed material is textile-like.

9. Process according to claim 1, wherein said processed material is fleece-like.

10. Process according to claim 1, wherein said processed material is mat-like.

11. Process according to claim 1, wherein said processed material is cloth-like.

12. Process according to claim 1, wherein said heat emission is detected from at least one direction.

13. Process according to claim 1, wherein said heat emission is detected from a plurality of directions.

14. Process according to claim 13, wherein the heat emission detection provides temperature data which are processed to provide a calculation of the amount of residual humidity in the thus-detected portion or the area of said thus-detected portion.

15. Process according to claim 1, wherein the detection of heat emission is carried out from above and from below the processed material being irradiated.

16. Process according to claim 1, wherein the thus-detected portions removed from said processed material by said sorting device are fed to a drying device for recycling.

17. Process according to claim 16, wherein said drying device is also controlled by said temperature data.

* * * * *